United States Patent [19]

Ozawa

[11] Patent Number: 5,472,454
[45] Date of Patent: Dec. 5, 1995

[54] LEAKAGE CURRENT BLOCKING CIRCUIT

[75] Inventor: Robert D. Ozawa, Valencia, Calif.

[73] Assignee: Pacesetter, Inc., Sylmar, Calif.

[21] Appl. No.: 234,901

[22] Filed: Apr. 28, 1994

[51] Int. Cl.[6] ................................................ A61N 1/39
[52] U.S. Cl. ..................................... 607/5; 607/63
[58] Field of Search ............................. 607/5, 63, 2, 4

[56] References Cited

U.S. PATENT DOCUMENTS

| | | | |
|---|---|---|---|
| 4,566,457 | 1/1986 | Stemple | 607/5 |
| 4,595,009 | 6/1986 | Leinders | 607/5 |
| 5,405,361 | 4/1995 | Persson | 607/5 |

*Primary Examiner*—William E. Kamm
*Assistant Examiner*—Kennedy J. Schaetzle
*Attorney, Agent, or Firm*—Lisa P. Weinberg

[57] ABSTRACT

A defibrillator circuit that uses one or more self-switching switches to prevent the flow of leakage current through a patient's heart is provided. When the voltage across a self-switching switch is below a predetermined threshold the self-switching switch is open, which directs leakage current through a bypass resistor rather than the patient's heart. When a defibrillation pulse is generated the voltage across the self-switching switch rises above the predetermined threshold of the self-switching switch, which turns on the self-switching switch and allows the defibrillation pulse to be applied to the patient's heart. A monophasic defibrillator operates with one self-switching switch and one bypass resistor. Two sets of self-switching switches and bypass resistors are used in a biphasic defibrillator.

31 Claims, 1 Drawing Sheet

LEAKAGE CURRENT BLOCKING CIRCUIT

BACKGROUND OF THE INVENTION

The present invention relates to cardiac defibrillators. More particularly, this invention is directed toward a blocking circuit that prevents an undesirable leakage current from being applied to a patient's heart when the patient is connected to a cardiac defibrillator for an extended period of time.

Cardiac defibrillators are devices that deliver high-voltage pulses to a patient's heart for the purpose of terminating an episode of cardiac fibrillation. Some defibrillators are used by physicians in emergencies - i.e., when a patient unexpectedly suffers an episode of cardiac fibrillation. Other types of defibrillator systems are used in different contexts. For example, some defibrillators are implanted within a patient, and continually monitor the patient's heart to determine whether the heart is fibrillating. If the heart begins to fibrillate, the implanted defibrillator will apply a defibrillation pulse to the heart to terminate the episode of fibrillation.

Defibrillators are used in yet another context when a physician wishes to adjust the voltage level at which an implanted defibrillator has been set to apply defibrillation pulses. The appropriate voltage level may vary considerably from patient to patient. For example, the voltage to be applied may depend on the condition of the defibrillator's leads, which are used to apply defibrillation pulses to the heart, as well as the characteristics of each individual's heart. As a result, before the appropriate defibrillation voltage level is selected for an implantable defibrillator, the physician will typically induce fibrillation in the patient's heart to determine what voltage level is required to terminate fibrillation for that patient. After attempting to terminate the fibrillation with pulses having low voltage levels, the physician will typically raise the level of the applied voltage until a level that is effective for terminating the episode is reached. Defibrillation systems used for this method of determining defibrillation thresholds are commonly known as defibrillator system analyzers.

Although defibrillator system analyzers may be used by physicians to determine a patient's defibrillation threshold, these analyzers must often be connected to the patient for extended periods of time to allow the physician to complete the threshold analysis. In order to reduce the likelihood of applying a leakage current to the patient, it would be desirable to provide a leakage current blocking circuit. An effective leakage current blocking circuit would help prevent leakage-current induced corrosion of the leads of those cardiac defibrillators that are implanted in a patient. The blocking circuit should be manufacturable in an efficient and cost-effective manner.

SUMMARY OF THE INVENTION

The disadvantages and limitations of previously known defibrillators are overcome by the present invention. With this invention, a defibrillator blocking circuit is provided for preventing defibrillator leakage currents. The blocking circuit is manufacturable in an efficient and cost-effective manner.

In a preferred embodiment of the present invention, the blocking circuit has a bypass resistor that is used to provide an alternate pathway for the defibrillator leakage current that would otherwise flow through the patient. The leakage current is prevented from passing though the patient by a self-switching semiconductor device, such as the self-switching switches known as a surgectors. The self-switching switch acts as an open circuit when the voltage across such a device is less than a predetermined threshold voltage. When a high-voltage defibrillating pulse is applied, the self-switching switch acts as a closed circuit, which allows the defibrillating pulse to pass to the patient. Preferably, the bypass resistor that is used has a sufficiently large resistance with respect to the resistance of the patient's body, so that only a negligible fraction of the energy of the defibrillation pulses is dissipated in the bypass resistor. The blocking circuit can preferably be used in either defibrillator system analyzers or in implantable defibrillators. In addition, the blocking circuit can be adapted for use with either monophasic or biphasic defibrillators.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Fibrillation is a dangerous cardiac condition in which the heart exhibits extremely rapid and irregular contractions. The devices used to terminate episodes of fibrillation are commonly known as defibrillators. Many defibrillators are designed for use by medical personnel in emergencies (i.e., when a patient unexpectedly suffers an episode of fibrillation). When it is known that a patient is at high risk of suffering from an episode of fibrillation, an implantable defibrillator may be surgically implanted in the patient's body, where it is attached to the heart via one or more electrical leads.

Implantable defibrillators are typically fairly sophisticated devices that allow a physician to tailor the strength of the high-voltage pulse that is supplied by the defibrillator to the individual needs of a patient. In order to ascertain the appropriate voltage setting, the physician may induce one or more episodes of fibrillation and subsequently apply defibrillation pulses of varying intensity. By observing which pulses successfully terminate fibrillation, the physician can determine the defibrillation threshold voltage. The physician can then adjust the settings of the implanted defibrillator so that the defibrillation pulses that the implanted defibrillator supplies will be slightly larger than the threshold. The specialized type of defibrillator used to apply defibrillation pulses when the physician is determining the defibrillation threshold voltage is known as a defibrillator system analyzer.

Figure 1:
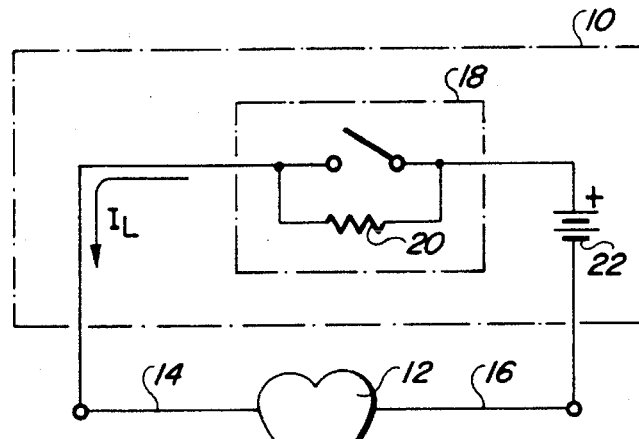
FIG. 1 is a circuit diagram of a prior art defibrillator that is connected to a patient's heart.

A defibrillator 10 without a leakage buffer circuit is shown in FIG. 1. The defibrillator 10 is connected to a patient's heart 12 via leads 14 and 16. Although the defibrillator 10 contains a conventional switch 18 that is capable of supporting high-voltage and high-power switching, the switch 18 has a parasitic resistance - represented by a resistor 20 - that allows a leakage current, $I_L$, to pass though the patient's heart 12 even when the switch 18 is open. The leakage current is produced because the output voltage of a conventional power supply 22 contained within the defibrillator 10 is typically extremely large - approximately 500 V. In defibrillators such as these with a standby emergency capability, the leakage current will be applied to the patient's heart 12 continuously.

Figure 2:
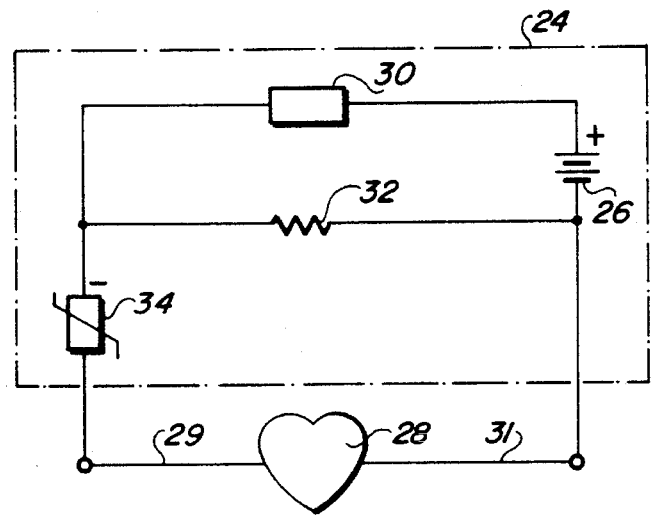
FIG. 2 is a circuit diagram of a preferred embodiment of the blocking circuit of the present invention for use with a monophasic defibrillator.

In order to protect the patient from the potential hazards caused by the leakage current, the arrangement of the present invention can be used, as shown in FIG. 2. The defibrillator 24 contains a conventional high-voltage power supply 26, which when powered, preferably supplies a voltage level of approximately 500 V. When it is desired to apply a monophasic high-voltage defibrillation pulse to a heart 28, a conventional high-voltage high-power switch 30, similar to the switch 18 shown in FIG. 1, is closed for a pulse length of approximately 2 ms to 10 ms by control circuitry (not shown). When the switch 30 is open, a leakage current from the switch 30 is present, but flows through a bypass resistor 32, rather than the heart 28. A self-switching switch 34 prevents the leakage current from passing through the heart 28 via leads 29 and 31.

Preferably, self-switching switch 34 is capable of supporting rapid switching times and high-current operation. One appropriate self-switching switch 34 is known as a surgector, which achieves self-switching using the semiconductor avalanche breakdown effect. Surgectors are available from various sources including Harris Semiconductor Corporation, of Melbourne, Fla.

When the voltage across the self-switching switch 34 is below a predetermined threshold of approximately 30 V, the self-switching switch 34 is off and current is effectively blocked from flowing through the self-switching switch 34. (A negligible leakage current of 50 nA flows though the self-switching switch 34 when off.) When the voltage across the self-switching switch 34 exceeds the predetermined threshold, the self-switching switch 34 turns on and the resistance of the self-switching switch 34 becomes negligible. The self-switching switch 34 preferably supports currents as high as approximately 50 A for as long as approximately 20 ms.

The resistance of a typical patient's heart 28 is in the range of from about 20 Ω to about 300 Ω. Preferably, the bypass resistor 32 has a resistance that is small enough that even a large leakage current will induce a voltage rise across the bypass resistor 32 (and therefore the self-switching switch 34) that remains below the threshold of the self-switching switch 34. For example, if a 100 λA leakage current is encountered and the resistance of the bypass resistor 32 is 10 KΩ, the voltage across the self-switching switch 34 will only rise to 1 V, which is well below the threshold voltage of 30 V that is required to turn the self-switching switch 34 on. Preferably, the bypass resistor 32 also has a resistance that is large enough to preclude a significant flow of defibrillation current from passing through the bypass resistor 32 during the application of a defibrillation pulse, because such current needlessly wastes pulse power. If the resistance of the patient's heart 28 is 100 Ω and the resistance of the bypass resistor 32 is 10 KΩ, then for the example above, approximately 99 per cent of the defibrillation pulse energy will be applied to the patient's heart 28.

Figure 3:
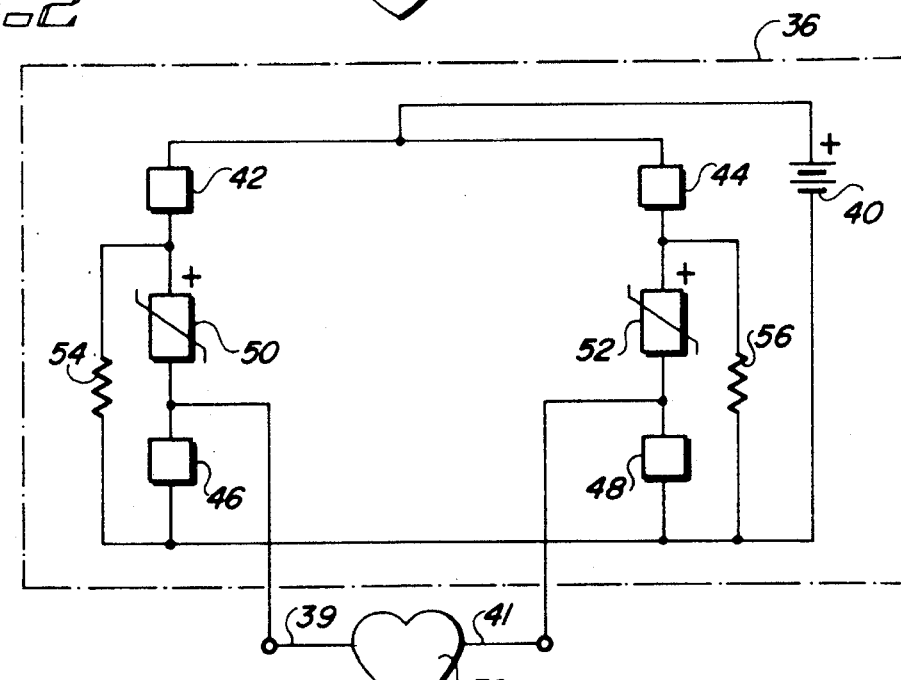
FIG. 3 is a circuit diagram of a preferred embodiment of the blocking circuit of the present invention for use with a biphasic defibrillator.

A biphasic defibrillator 36 with circuitry for preventing the application of leakage current to a patient's heart 38 is shown in FIG. 3. A conventional power supply 40 is preferably capable of providing a 500 V defibrillation pulse to the patient's heart 38 via leads 39 and 41. The defibrillator 36 contains conventional high-voltage high-power switches 42, 44, 46 and 48 (each preferably identical to the switch 30 shown in FIG. 2). To apply a biphasic pulse to the patient's heart 38, a first half of the pulse is applied by closing the switches 42 and 48 for 2 ms to 15 ms while the switches 44 and 46 are held open. Because the voltage across self-switching switch 50 exceeds the threshold necessary to turn it on, the first half of the pulse passes to the patient's heart 38. A second half of the pulse is applied by closing switches 44 and 46 while the switches 42 and 48 are held open, which causes self-switching switch 52 to turn on. When pulses are not being applied to the patient, the switches 42, 44, 46 and 48 are open. Leakage current through the switches 42 and 44 is prevented from flowing through the patient's heart 38 by the self-switching switches 50 and 52, passing instead through the bypass resistors 54 and 56. Thus it is seen that a defibrillator circuit that uses one or more self-switching switches to prevent the flow of leakage current through a patient's heart has been provided. When the voltage across a self-switching switch is below a predetermined threshold the self-switching switch is open, which directs leakage current through a bypass resistor rather than the patient's heart. When a defibrillation pulse is generated the voltage across the self-switching switch rises above the predetermined threshold of the self-switching switch, which turns on the self-switching switch and allows the defibrillation pulse to be applied to the patient's heart. A monophasic defibrillator operates with one self-switching switch and one bypass resistor. Two sets of self-switching switches and bypass resistors are used in a biphasic defibrillator. One skilled in the art will appreciate that the present invention can be practiced by other than the described embodiments, which are presented for purposes of illustration and not of limitation, and the present invention is limited only by the claims that follow.

What is claimed is:

1. A defibrillator for applying a defibrillation pulse to a patient's heart to which the defibrillator is connected, the defibrillator comprising:

a power supply;

a high-voltage switch connected to the power supply such that a leakage current flows through the high-voltage switch when the high-voltage switch is off;

a bypass resistor connected between the high-voltage switch and the power supply; and a self-switching switch connected between the resistor and the heart for preventing the leakage current from being applied to the heart and allowing the defibrillation pulse to be applied to the heart; wherein:

(a) when the high-voltage switch is off:
   the leakage current flows through the high-voltage switch and the bypass resistor, and
   there is a first voltage across the self-switching switch that is below a predetermined threshold voltage, so that the self-switching switch is off and the leakage current is prevented from flowing through the self-switching switch to the heart; and (b) when the high-voltage switch is on:
   there is a second voltage across the self-switching switch that is above the predetermined threshold voltage, so that the self-switching switch is on and the defibrillation pulse is allowed to pass through the self-switching switch and to the heart.

2. The defibrillator of claim 1, wherein the self-switching switch comprises a surgector.

3. The defibrillator of claim 1, wherein the defibrillating pulse is monophasic.

4. The defibrillator of claim 3, wherein the defibrillating pulse is biphasic.

5. The defibrillator of claim 1, further comprising:
   a first lead connected between the heart and the power supply; and
   a second lead connected between the self-switching switch and the heart.

6. A biphasic defibrillator for applying a biphasic defibrillation pulse to a patient's heart to which the defibrillator is connected, the defibrillator comprising:
   a power supply having first and second power-supply terminals;
   first, second, third and fourth high-voltage switches, the first and second high-voltage switches being connected to the first power supply terminal such that first and second leakage currents flow through the first and second high-voltage switches, respectively, when the first and second high-voltage switches are off, and the third and fourth high-voltage switches being connected to the second power supply terminal;
   a first bypass resistor connected between the first switch and the power supply;
   a second bypass resistor connected between the second switch and the power supply;
   a first self-switching switch connected between the first resistor and the heart; and
   a second self-switching switch connected between the second resistor and the heart, the first and second self-switching switches preventing the first and second leakage currents, respectively, from being applied to the heart and allowing the defibrillation pulse to be applied to the heart; wherein:
   (a) when the first, second, third and fourth high-voltage switches are off:
      the first leakage current flows through the first high-voltage switch and the first bypass resistor,
      the second leakage current flows through the second high-voltage switch and the second bypass resistor,
      there is a first voltage across the first self-switching switch that is below a first predetermined threshold voltage, so that the first self-switching switch is off, and the first leakage current is prevented from flowing through the first self-switching switch to the heart, and
      there is a second voltage across the second self-switching switch that is below a second predetermined threshold voltage, so that the second self-switching switch is off, and the second leakage current is prevented from flowing through the second self-switching switch to the heart; and
   (b) when the first and fourth high-voltage switches are on and the second and third high-voltage switches are off:
      there is a third voltage across the first self-switching switch that is above the first predetermined threshold voltage, so that the first self-switching switch is on, and a first portion of the defibrillation pulse is allowed to pass through the first self-switching switch and to the heart; and
   (c) when the second and third high-voltage switches are on and the first and fourth high-voltage switches are off:
      there is a fourth voltage across the second self-switching switch that is above the second predetermined threshold voltage, so that the second self-switching switch is on, and a second portion of the defibrillation pulse is allowed to pass through the second self-switching switch and to the heart.

7. The defibrillator of claim 6, wherein the first and second self-switching switches comprise surgectors.

8. The defibrillator of claim 6, wherein the defibrillation pulse has a defibrillation pulse power, such that when the defibrillation pulse is allowed to pass through the first and second self-switching switches, at least 99 percent of the defibrillation pulse power is applied to the heart and at most one percent of the defibrillation pulse power is dissipated in the first and second bypass resistors.

9. The defibrillator of claim 6, wherein the first and second bypass resistors have essentially equivalent resistances.

10. The defibrillator of claim 6, wherein the first and second predetermined thresholds are essentially equivalent.

11. The defibrillator of claim 6, wherein the first and second voltages are essentially equivalent.

12. The defibrillator of claim 6, wherein the third and fourth voltages are essentially equivalent.

13. A method for applying a defibrillation pulse to a patient's heart with a defibrillator that has a power supply and a high-voltage switch connected to the power supply such that a leakage current flows through the high-voltage switch when the high-voltage switch is off, comprising the steps of:
   connecting a bypass resistor between the high-voltage switch and the power supply;
   preventing the leakage current from being applied to the heart by placing a self-switching switch between the resistor and the heart;
   allowing the leakage current to flow through the high-voltage switch and the bypass resistor when the high-voltage switch is off;
   preventing the leakage current from flowing through the self-switching switch and the heart when the high-voltage switch is off; and
   applying a defibrillation pulse to the heart via the self-switching switch when the high-voltage switch is on.

14. The method of claim 13, wherein the step of preventing the leakage current from flowing through the self-switching switch comprises the step of maintaining a voltage across the self-switching switch below a predetermined threshold voltage.

15. The method of claim 14, wherein the step of preventing the leakage current from flowing through the self-switching switch comprises the step of using a surgector as the self-switching switch.

16. The method of claim 13, wherein the step of applying the defibrillation pulse comprises the step of applying a monophasic defibrillation pulse to the heart.

17. The method of claim 13, wherein the step of applying the defibrillation pulse comprises the step of applying a biphasic defibrillation pulse to the heart.

18. The method of claim 13, wherein:
   the defibrillation pulse has a pulse power; and
   the step of applying the defibrillation pulse via the self-switching switch comprises the step of applying at least 99 percent of the defibrillation pulse power to the heart and at most one percent of the defibrillation pulse power to the bypass resistor.

19. The method of claim 13, wherein the step of applying the defibrillation pulse via the self-switching switch comprises the steps of:

connecting the power supply to the heart with a first lead; and connecting the self-switching switch to the heart with a second switch.

20. A method for applying a biphasic defibrillation pulse to a patient's heart with a biphasic defibrillator, comprising the steps of:

providing a high voltage with a power supply;

applying a first phase of the biphasic pulse to the heart with first and third high-voltage switches that are on and a first self-switching switch that is on;

applying a second phase of the biphasic pulse to the heart with second and fourth high-voltage switches that are on and a second self-switching switch that is on; and preventing leakage current from flowing through the first, second, third and fourth high-voltage switches when the first, second, third and fourth high-voltage switches are off.

21. The method of claim 20, wherein the step of preventing leakage current from flowing through the first, second, third and fourth high-voltage switches comprises the steps of:

connecting a first bypass resistor between the first switch and the power supply; and connecting a second bypass resistor between the second switch and the power supply.

22. The method of claim 20, wherein the step of preventing leakage current from flowing through the first, second, third and fourth high-voltage switches comprises the steps of:

connecting the first self-switching switch between the first resistor and the heart; and connecting the second self-switching switch between the second resistor and the heart.

23. The method of claim 22, wherein the steps of connecting the first and second self-switching switches comprise the steps of connecting first and second surgectors.

24. The method of claim 21, wherein when the defibrillation pulse is applied at least 99 percent of the defibrillation pulse power is applied to the heart and at most one percent of the defibrillation pulse power is dissipated in the first and second bypass resistors.

25. A defibrillator for applying a defibrillation pulse to a patient's heart to which the defibrillator is connected, comprising:

a power supply;

a high-voltage switch connected to the power supply such that a leakage current to the patient's heart flows through the high-voltage switch when the high-voltage switch is off; and a self-switching leakage buffer for preventing the flow of the leakage current when the high-voltage switch is off and for allowing the defibrillation pulse to be applied to the heart when the high-voltage switch is on.

26. The defibrillator of claim 25, wherein the self-switching leakage buffer comprises:

bypass resistor connected between the high-voltage switch and the power supply; and a self-switching switch connected between the resistor and the heart, wherein:

(a) when the high-voltage switch is off:

the leakage current flows through the high-voltage switch and the bypass resistor, and there is a first voltage across the self-switching switch that is below a predetermined threshold voltage, so that the self-switching switch is off and the leakage current is prevented from flowing through the self-switching switch to the heart; and (b) when the high-voltage switch is on:

there is a second voltage across the self-switching switch that is above the predetermind threshold voltage, so that the self-switching switch is on and the defibrillation pulse is allowed to pass through the self-switching switch and to the heart.

27. The defibrillator of claim 26, wherein the self-switching switch comprises a surgector.

28. The defibrillator of claim 26, wherein the defibrillating pulse is monophasic.

29. The defibrillator of claim 26, wherein the defibrillating pulse is biphasic.

30. The defibrillator of claim 26, wherein the defibrillation pulse has a defibrillation pulse power and the bypass resistor has a resistance, such that when the defibrillation pulse is allowed to pass through the self-switching switch, at least 99 percent of the defibrillation pulse power is applied to the heart and at most one percent of the defibrillation pulse power is dissipated in the bypass resistor.

31. The defibrillator of claim 26, further comprising:

a first lead connected between the heart and the power supply; and a second lead connected between the self-switching switch and the heart.

* * * * *